United States Patent [19]

Suzuki et al.

[11] Patent Number: 5,604,781
[45] Date of Patent: Feb. 18, 1997

[54] MEDICAL X-RAY IMAGING APPARATUS

[75] Inventors: Masakazu Suzuki; Keisuke Mori; Akifumi Tachibana; Kazunari Matoba, all of Kyoto; Hitoshi Asai; Kazuhisa Miyaguchi, both of Hamamatsu; Toshitaka Takeguchi, Shizuoka, all of Japan

[73] Assignees: J. Morita Manufacturing Corporation, Kyoto; Hamamatsu Photonics Kabushiki Kaisha, Shizuoka, both of Japan

[21] Appl. No.: 598,440

[22] Filed: Feb. 8, 1996

[30]   Foreign Application Priority Data

Feb. 9, 1995   [JP]   Japan ................................ 7-022146

[51] Int. Cl.⁶ ................................................ G01N 23/04
[52] U.S. Cl. ................................ 378/62; 378/901
[58] Field of Search .................... 378/62, 98.12, 378/901

[56]                References Cited

U.S. PATENT DOCUMENTS 5,452,338   9/1995  Granfors et al. ................ 378/98.11
5,541,974   7/1996  Sklebitz ........................... 378/98.8

FOREIGN PATENT DOCUMENTS 61-22481    1/1986   Japan .
62-43990    2/1987   Japan .
4-48169    11/1992   Japan .

*Primary Examiner*—David P. Porta
*Assistant Examiner*—David Vernon Bruce
*Attorney, Agent, or Firm*—Koda and Androlia

[57]                ABSTRACT

The present invention provides an X-ray tomographic imaging apparatus, wherein image degrading components caused by a CCD sensor (3c) or the like are reduced so as to obtain high-quality X-ray images. After tomographic imaging, dark current noise is eliminated by subtracting dark current correction data from a specific line of data among image data stored in an image memory. Next, sensitivity correction coefficients are prepared on the basis of data obtained when an X-ray beam having nearly uniform intensity distribution enters an X-ray imaging device 3. The image data obtained after dark current correction is then multiplied by the sensitivity correction coefficients. As a result, noise due to sensitivity variations or the like can be eliminated.

7 Claims, 5 Drawing Sheets

FIG.5(a)
ORIGINAL DATA

| 1 | 50 |
| 2 | 64 |
| 3 | 85 |
| 4 | 100 |
| 5 | 142 |
| 6 | 190 |
| 7 | 226 |
| ⋮ | ⋮ |
| n-1 | 152 |
| n | 114 |

FIG.5(b)
DARK CURRENT

| 1 | 0 |
| 2 | 0 |
| 3 | 4 |
| 4 | 3 |
| 5 | 2 |
| 6 | 0 |
| 7 | 2 |
| ⋮ | ⋮ |
| n-1 | 0 |
| n | 1 |

FIG.5(c)
AFTER DARK CURRENT CORRECTION

| 1 | 50 |
| 2 | 64 |
| 3 | 81 |
| 4 | 97 |
| 5 | 140 |
| 6 | 190 |
| 7 | 224 |
| ⋮ | ⋮ |
| n-1 | 152 |
| n | 113 |

FIG.5(d)
UNIFORM IRRADIATION

| 1 | 102 |
| 2 | 104 |
| 3 | 100 |
| 4 | 108 |
| 5 | 96 |
| 6 | 97 |
| 7 | 101 |
| ⋮ | ⋮ |
| n-1 | 104 |
| n | 100 |

FIG.5(e)
SENSITIVITY CORRECTION COEFFICIENT

| 1 | 100/102 |
| 2 | 100/104 |
| 3 | 1 |
| 4 | 100/108 |
| 5 | 100/96 |
| 6 | 100/97 |
| 7 | 100/101 |
| ⋮ | ⋮ |
| n-1 | 100/104 |
| n | 1 |

FIG.5(f)
AFTER DARK CURRENT CORRECTION AND SENSITIVITY CORRECTION

| 1 | 49 |
| 2 | 62 |
| 3 | 81 |
| 4 | 90 |
| 5 | 146 |
| 6 | 196 |
| 7 | 222 |
| ⋮ | ⋮ |
| n-1 | 146 |
| n | 113 |

MEDICAL X-RAY IMAGING APPARATUS

BACKGROUND OF THE INVENTION

1. Field of the Invention

The present invention relates to a medical X-ray imaging apparatus for taking tomograms along desired tomographic planes of subjects, such as the head, body, and hands and legs of a human body.

2. Description of the Related Art

As related arts, Japanese Laid-open Patent Application No. Sho 61-22841 and Utility Model Registration Publication No. Hei 4-48169 disclose an X-ray imaging apparatus for performing TDI (Time Delay Integration) of an image signal by changing the frequency of a charge transfer clock signal in accordance with the movement of an X-ray image formed on a CCD sensor while being moved.

In addition, Japanese Laid-open Patent Application No. Sho 62-43990 discloses a method and an apparatus for X-ray imaging by scanning a charge pattern corresponding to X-ray intensity distribution in a space by using an electrometer after X-ray imaging, wherein artifacts (artificial images) are reduced by correcting the X-ray image.

However, in the above-mentioned related arts, when dark current noise, variations in sensitivity, etc. occur in the CCD sensor, artificial images are generated in the X-ray image taken by an X-ray imaging apparatus, causing not only reduction in image quality and resolution but also the danger of erroneous diagnosis. Furthermore, since numerous light-receiving pixels are formed on the CCD sensor, the manufacturing yield of such CCD sensors is lowered extremely when an attempt is made to obtain CCD sensors having small variations in performance, eventually resulting in higher cost.

Furthermore, in Japanese Laid-open Patent Application No. Sho 62-43990, signal processing different from that of the TDI method is performed by using a special X-ray imaging device referred to as an X-ray converting photoconductor made selenium. It is therefore considerably difficult to directly apply the image correction method used for the special signal processing to the TDI method.

SUMMARY OF THE INVENTION

The object of the present invention is to provide a medical X-ray imaging apparatus capable of obtaining high-quality X-ray images by reducing image quality degrading components caused by a CCD sensor or the like.

The invention relates to a medical X-ray imaging apparatus comprising:

an X-ray generator for emitting X-rays toward a subject,
an X-ray imaging device for detecting an X-ray image passed through the subject;
a swivel member for rotating the X-ray generator and the X-ray imaging device disposed opposite to each other around the subject;
an image memory for storing an image signal from the X-ray imaging device; and
means for displaying the image signal stored in the image memory, wherein
the X-ray imaging device contains CCD sensors, each having a plurality of light-receiving pixels arranged in two dimensions, and takes the image of a predetermined tomographic plane by changing the frequency of a charge transfer clock signal depending on the rotation speed of the swivel member, characterized in that the X-ray imaging apparatus is provided with:

a first reference memory for storing as first correction data at least one line of data from the signal outputted from the X-ray imaging device and obtained when the X-ray imaging device is operated with no X-ray beam entry; and a second reference memory for storing as second correction data at least one line of data from the signal outputted from the X-ray imaging device and obtained when the X-ray imaging device is operated while an X-ray beam having nearly uniform intensity distribution enters the X-ray imaging device, and that the image signal is corrected by addition or subtraction by using the first correction data stored in the first reference memory or by performing multiplication or division by using the second correction data stored in the second reference memory.

Furthermore, in the invention, the image signal outputted from the X-ray imaging device is corrected.

Furthermore, in the invention, the image signal stored in the image memory is corrected.

Furthermore, in the invention, the image signal outputted from the image memory to the display means is corrected.

Furthermore, in the invention, the first reference memory stores the correction data for the entire screen image included in the signal outputted from the X-ray imaging device.

Furthermore, in the invention, signal correction is performed after the correction data of the first reference memory is corrected in accordance with the temperature detected by a temperature sensor provided to detect the temperature of the X-ray imaging device.

Furthermore, in the invention, signal correction is performed after the correction data of the first reference memory is corrected in accordance with the staying time of signal charges in a vertical shift register of the CCD sensor.

In accordance with the invention, the signal outputted from the X-ray imaging device and obtained when the X-ray imaging device is operated with no X-ray beam entry is noise caused by the dark current or this like of the CCD sensor. At least one line of data from the signal is stored beforehand in the first reference memory as the first correction data. The first correction data stored in the first reference memory is added to or subtracted from the image signal obtained by ordinary X-ray tomographic imaging to eliminate the noise components from the image signal, thereby affording a tomographic image having a high S/N ratio.

Furthermore, the signal outputted from the X-ray imaging device and obtained when the X-ray imaging device is operated while an X-ray beam having a nearly uniform intensity distribution enters is noise caused by the variations in the image sensitivity of the CCD sensor. At least one line of data from the signal is stored beforehand in the second reference memory as the second correction data. The image signal obtained by ordinary X-ray tomographic imaging is then multiplied or divided by using the second correction data stored in the second reference memory to eliminate the noise components from the image signal, thereby affording a high-quality tomographic image having few artificial images. Either the signal correction by using the first correction data or the signal correction by using the second correction data may be used, or both may be used.

Furthermore, by correcting the image signal being outputted every moment from the X-ray imaging device during X-ray imaging, signal correction can be completed at the end of X-ray imaging. It is thus possible to shift promptly to image display operation.

Furthermore, by correcting the image signal having been stored once in the image memory, arithmetic operation for signal correction can be made at a low speed, thereby reducing the load on the processing circuits.

Furthermore, by correcting the image signal outputted from the image memory to the display means, correction can be performed while the image before correction is compared appropriately with the image after correction, thereby enabling optimization of signal correction.

Furthermore, by storing the correction data for the entire image included in the signal outputted from the X-ray imaging device, the first reference memory allows more accurate signal correction.

Furthermore, since the dark current of the CCD sensor depends on temperature, more accurate signal correction can be performed by measuring the temperature of the CCD sensor with the temperature sensor provided close to the X-ray imaging sensor and by correcting the correction data stored in the first reference memory in consideration of the deviation between the temperature at the time of the preparation of the correction data and the temperature during X-ray imaging.

Furthermore, the dark current of the CCD sensor is apt to increase when the time during which the signal charges stay in a vertical shift register is prolonged. By correcting the correction data of the first reference memory depending on the staying time, more accurate signal correction can be attained.

As detailed above, since noise caused by the dark current and sensitivity variations or the like of the CCD sensor can be eliminated from the image signal obtained by X-ray tomographic imaging, a high-quality tomographic image having a high S/N ratio and few artificial images can be obtained.

Furthermore, since a considerable amount of noise can be eliminated by electrical signal correction, variations in the characteristics of the CCD sensor are kept smaller. Therefore, the manufacturing yield of the sensors can be improved and the cost can be reduced.

Furthermore, by measuring the temperature of the X-ray imaging device with the temperature sensor, signal correction can be performed effectively even when the image signal includes noise being dependent on temperature.

BRIEF DESCRIPTION OF THE DRAWINGS

Other and further objects, features, and advantages of the invention will be more explicit from the following detailed description taken with reference to the drawings wherein:

FIGS. 5a to 5f are schematic views showing concrete examples of signal correction operation.

DETAILED DESCRIPTION OF THE PREFERRED EMBODIMENTS

Figure 1:
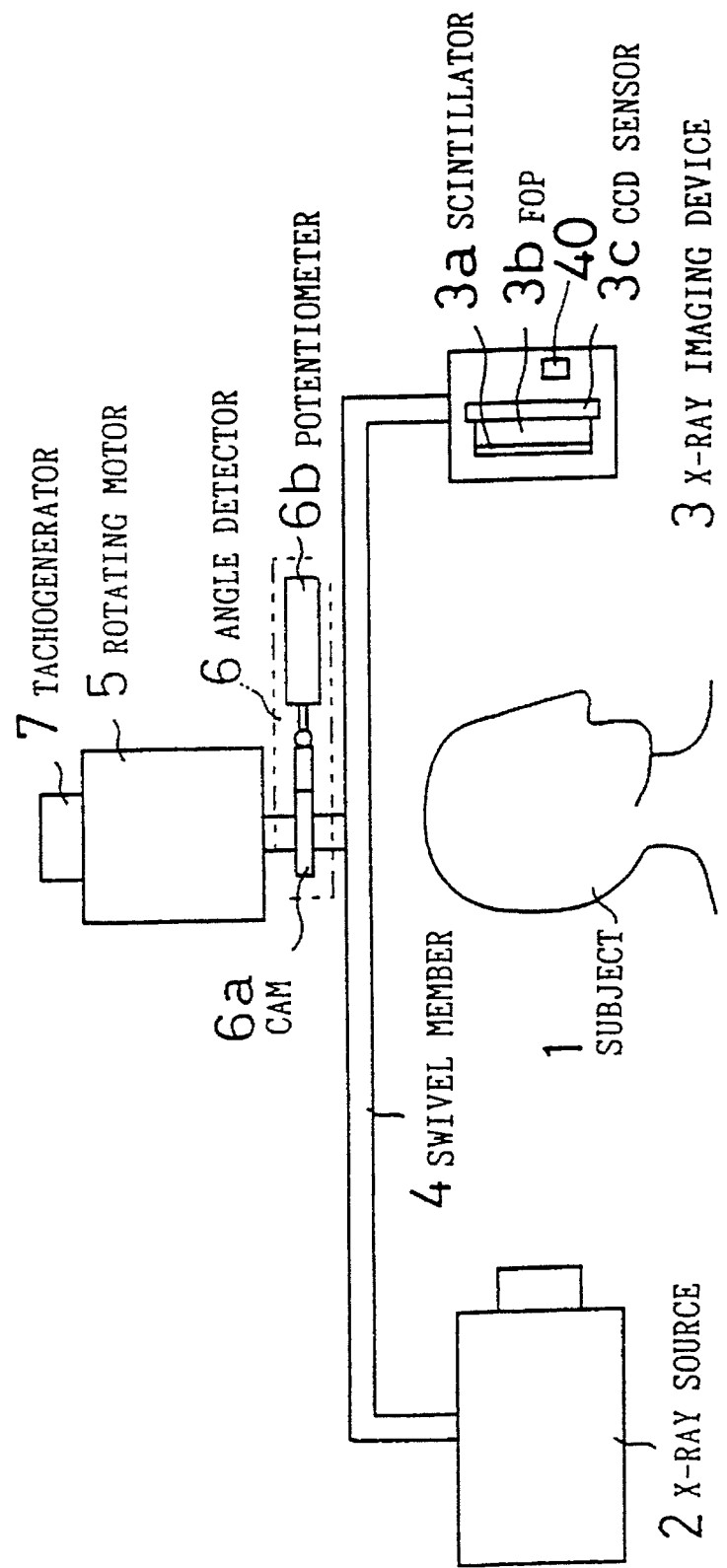
FIG. 1 is a structural view showing an embodiment of the invention.

Now referring to the drawings, preferred embodiments of the invention are described below.

FIG. 1 is a structural view showing an embodiment of the invention. The medical X-ray imaging apparatus of the invention comprises an X-ray source 2 for generating a vertical slit-shaped X-ray beam, an X-ray imaging device 3 for detecting an X-ray image having passed through a subject 1, and a swivel member 4 for holding the X-ray source 2 and the X-ray imaging device 3 disposed opposite to each other and for rotating the X-ray source 2 and the X-ray imaging device 3 around the subject 1.

The X-ray imaging device 3 comprises a scintillator 3a for converting an X-ray image obtained by an incoming X-ray beam into a visible light image, a fiber optic plate (FOP) 3b for guiding the visible light image from the scintillator 3a and a CCD (charge-coupled device) sensor 3c for imaging the visible light image from the fiber optic plate 3b. A temperature sensor 40 for measuring the temperature of the CCD (charge-coupled device) sensor 3c is disposed inside the X-ray imaging device 3.

A swivel member 4 (such as a rotary arm) is supported so as to be rotatable on a horizontal plane around the position just above the subject 1. The rotation shaft of the swivel member 4 is driven by a rotating motor 5. To detect the angular speed of the rotation shaft, a tachogenerator 7 is provided. Furthermore, a cam 6a mounted on the rotation shaft and a potentiometer 6b for detecting the displacement of the cam 6a constitute an angle detector 6.

Figure 2A:
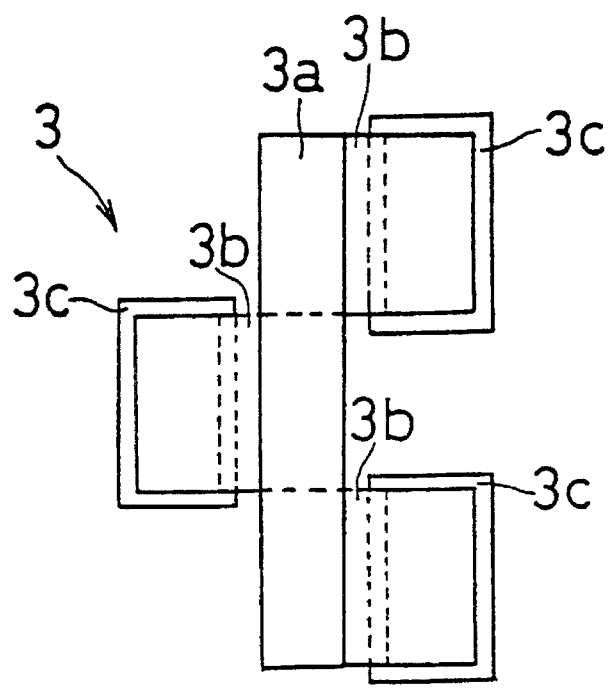
FIG. 2a is a front view showing the shape of an X-ray imaging device 3 and FIG. 2b is a bottom view of the X-ray imaging device.
Figure 2B:
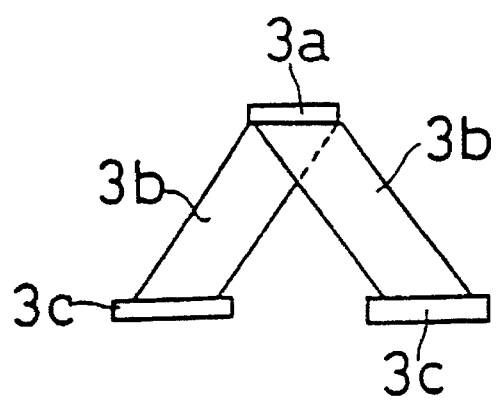

FIG. 2a is a front view showing the shape of the X-ray imaging device 3 and FIG. 2b is a bottom view of the device. The scintillator 3a is made slender so as to receive a vertical slit-shaped X-ray beam. A secondary slit (not shown) for limiting the light-receiving region of the X-ray imaging device 3 is provided on the X-ray incoming side. The optic fiber plate 3b has a parallelogram shape in cross section. The X-ray incoming surface of the plate 3b makes close contact with the scintillator 3a and the X-ray outgoing surface of the plate 3b is formed away from the passage of the X-ray beam having passed through the scintillator 3a. Although it is most preferred that the light-receiving region of the scintillator 3a is imaged by using a single CCD sensor 3c, when the CCD sensor 3c becomes larger in size, its cost increases because of its low manufacturing yield. To solve this problem, the light-receiving region is separated into three portions by using three CCD sensors, for example, as shown in FIG. 2 and a visible light image is taken. Accordingly, the fiber optic plate 3b is separated into three portions in accordance with the number of the CCD sensors 3c and these three portions are distributed to the right and left sides in a staggered arrangement from the view point of convenience in arrangement. The incoming slit-shaped X-ray beam is about 6 mm in width and 150 mm in length, and the light-receiving surface of the CCD sensor 3c is about 50 mm in length.

Figure 3:
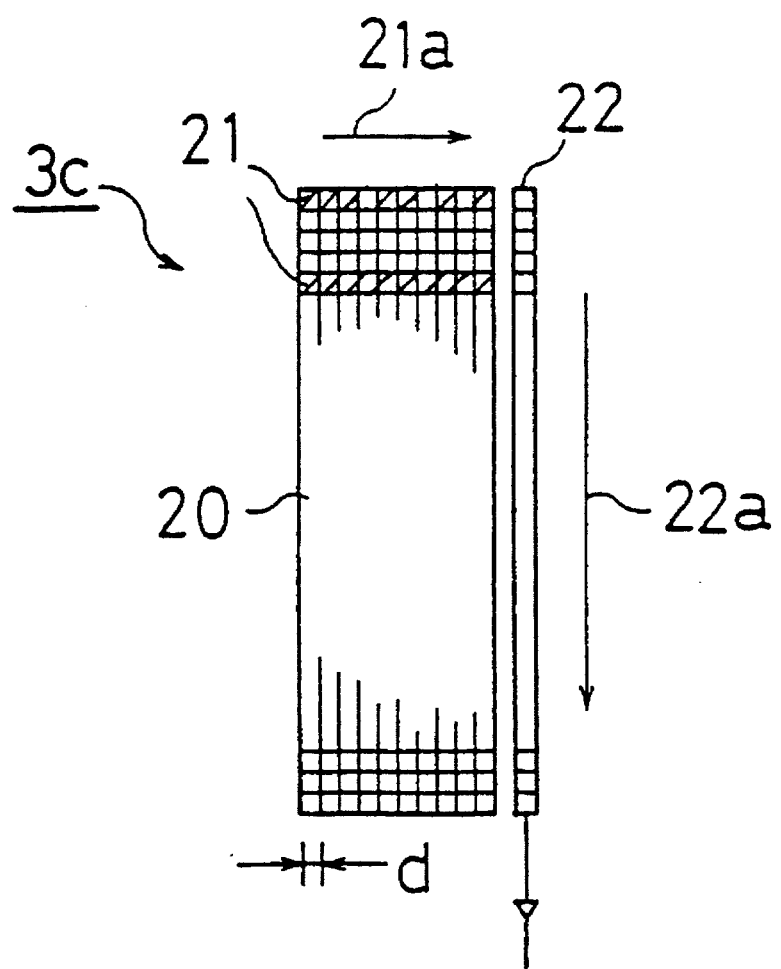
FIG. 3 is an arrangement view showing the pixel array and the charge transfer operation of a CCD sensor 3c.

FIG. 3 is an arrangement view showing the pixel array and the charge transfer operation of the CCD sensor 3c. The vertically long light-receiving portion 20 of the CCD sensor 3c comprises a plurality of light-receiving pixels arranged in a two-dimensional matrix. When a visible light image from the fiber optic plate 3b enters the light-receiving portion 20, charges are generated by photoelectric conversion. Each light-receiving pixel is electrically connected to a plurality of vertical shift registers 21 (shaded portions in FIG. 3) arranged in a horizontal direction 21a. In each vertical shift register 21, charges are transferred sequentially in the horizontal direction 21a in accordance with the charge transfer clock signal. The output portion of each vertical shift register 21 is electrically connected to horizontal shift registers 22 arranged in the vertical direction 22a so as to transfer all charges to the outside each time each vertical shift register 21 completes transfer for one pixel. In this way, the X-ray image is converted into a time series electric signal by the combination of horizontal and vertical scanning. Although the CCD sensor 3c shown in FIG. 3 is a full frame transfer (FFT) type having no charge storage portion, a frame transfer (FT) type having charge storage portions as many as the light-receiving pixels may be applied in the invention.

Next, the TDI operation of the CCD sensor 3c will be described. When the swivel member 4 rotates, the X-ray image is moved in the horizontal direction 21a. The movement speed of the X-ray image differs depending on the position of an X-ray tomographic plane. Therefore, by changing the charge transfer speed, that is, the frequency of the charge transfer clock signal of the vertical shift register 21, so as to coincide with the movement speed of the X-ray image corresponding to a predetermined tomographic plane, only the charges due to a desired X-ray tomographic image can be stored (integrated) sequentially as the charges are transferred. In this way, only the X-ray image coinciding with a specific charge transfer speed is taken as a still image, and X-ray images not coinciding with the charge transfer speed are left running. As a result, a tomographic image similar to that obtained by using a film in a conventional tomographic imaging apparatus can be obtained. When the frequency of the charge transfer clock signal is f, when the film feeding speed in the conventional tomographic imaging apparatus using films is v, and when the pixel spacing of the CCD sensor 3c is d, the equation of f=v/d is established.

Figure 4:
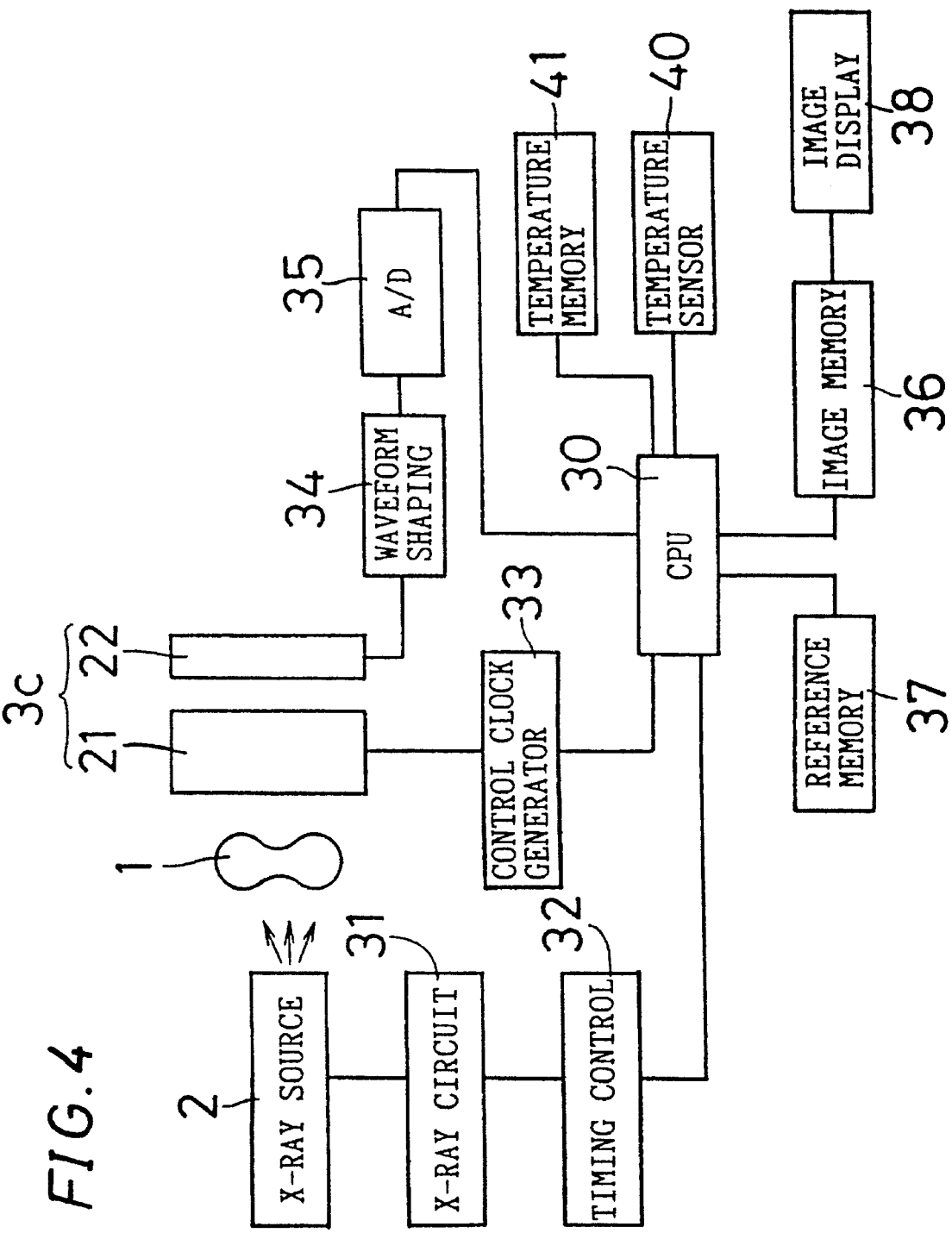
FIG. 4 is a block diagram showing an electrical configuration in accordance with an embodiment of the invention.

FIG. 4 is a block diagram showing an electrical configuration in accordance with an embodiment of the invention. The X-ray source 2 comprises an X-ray tube, for example. Electric power is supplied from an X-ray circuit 31 so as to drive the X-ray tube at a predetermined tube voltage and tube current. A timing control circuit 32 controls X-ray irradiation time in accordance with instructions from a CPU (central processing unit).

The vertical shift registers 21 and the horizontal shift register 22 of the CCD sensor 3c are driven by the vertical transfer clock signal and the horizontal transfer clock signal from a control clock generation circuit 33, respectively, and the frequency of each clock signal is changed depending on the rotation speed of the swivel member 4 in accordance with instructions from the CPU 30, thereby attaining the TDI operation. The horizontal shift register 22 of the CCD sensor 3c outputs the image signal of the X-ray tomographic image on the time series. The image signal thus obtained is subjected to waveform shaping by a waveform shaping circuit 34, converted into an 8-bit digital signal (having 256 levels), for example, by an analog/digital (A/D) conversion circuit 35, and stored in an image memory 36 via the CPU 30. The image signal stored in the image memory 36 is indicated on an image display apparatus 38, such as a CRT (cathode-ray tube) display or an image printer and is used for a variety of diagnoses.

In the medical X-ray imaging apparatus structured as described above, a reference memory 37 for storing various data for correcting the image signal and a temperature sensor 40 for measuring the temperature of the CCD sensor 3c are provided. The temperature sensor 40 can be provided in a chip in which the CCD sensor 3c is included.

FIGS. 5a to 5f are schematic views showing concrete examples of signal correction operation. A plurality of regions each capable of storing at least one line of data along the vertical direction (rotation shaft direction) of the X-ray imaging device 3 are prepared in the reference memory 37, and the image data before and after correction and correction data are stored. n is assigned to the number of pixels for one line.

First, FIG. 5a indicates data for a specific line of the image data of the X-ray tomographic image stored in the image memory 36 after tomographic imaging. n pieces of data, that is, 50 (decimal notation, identical hereinafter), 64, 85, 100, 142, 190, 226, ..., 152 and 114, from top to bottom, are original data before correction.

FIG. 5b indicates a predetermined line of data of the signal outputted from the X-ray imaging device 3 and obtained when the same operation as the tomographic imaging operation is performed with the X-ray source 2 stopped and when the X-ray imaging device 3 is operated with no X-ray beam entry. The data corresponds to noise caused by the dark current or the like of the CCD sensor 3c. n pieces of data, that is, 0, 0, 4, 3, 2, 0, 2 . . . , 0 and 1, from top to bottom, are stored in part of the reference memory 37 as dark current correction data. Once the dark current correction data is stored immediately after the installation of the apparatus or at the time of a periodical inspection, the same data can be used for all imaging operations. Alternatively, such data may be prepared at each imaging operation.

FIG. 5c indicates the result obtained by subtracting the dark current correction data shown in FIG. 5b from the original data shown in FIG. 5a. n pieces of data, that is, 50, 64, 81, 97, 140, 190, 224, . . . , 152 and 113, from top to bottom, are obtained as image data after dark current correction. By performing this kind of signal correction for each line of data, dark current correction can be attained for the entire screen image. Signal correction by subtraction is illustrated herein as an example. However, when the dark current correction data indicated in FIG. 5b is stored as negative values, signal correction is performed by addition. Subtraction or addition is adopted so as to reduce the noise. In this way, dark current noise components can be eliminated from the image signal.

FIG. 5d indicates a predetermined line of data of the signal outputted from the X-ray imaging device 3 and obtained when tomographic imaging is performed by operating the X-ray source 2 without the subject 1 and when an X-ray beam having nearly uniform intensity distribution enters the X-ray imaging device 3. Although the values of the data should preferably be the same fundamentally, fluctuations occur due to noise caused by variations in the pixel sensitivity of the CCD sensor 3c and nonuniform X-ray intensity distribution. n pieces of data, that is, 102, 104, 100, 108, 96, 97, 101 , . . . , 104 and 100, from top to bottom, are stored in part of the reference memory 37 as sensitivity variation correction data. The X-ray intensity used to measure sensitivity variations should preferably be limited to about half the intensity used during ordinary imaging to prevent data saturation. To attain this purpose, for example, the tube voltage or tube current of the X-ray source 2 is adjusted, or an aluminum plate having a uniform thickness (for example, 30 mm) is used as an X-ray attenuating filter instead of the subject 1.

FIG. 5e indicates sensitivity correction coefficients (real numbers), each of which is obtained for each pixel by calculating the ratio of the data indicated in FIG. 5d to the average value. It is assumed herein that the average value is 100. Therefore, n pieces of data, that is, 100/102, 100/104, 1, 100/108, 100/96, 100/97, 100/101, . . . , 100/104 and 1, from top to bottom, are stored in part of the reference memory 37 as sensitivity correction data. Once the sensitivity correction data is prepared immediately after the installation of the apparatus or at the time of periodical inspection, the same data can be used for all imaging operations. Alternatively, such data may be prepared at each imaging operation.

FIG. 5f indicates the values obtained by multiplying the image data obtained after dark current correction by the sensitivity correction coefficients shown in FIG. 5e and then by rounding off the decimal fractions of the values obtained by the multiplication. As a result, n pieces of data, that is, 49, 62, 81, 90, 146, 196, 222 , . . . , 146 and 113, from top to bottom, are obtained as image data after sensitivity correction. By performing this kind of signal correction for all lines of the image data, the sensitivity correction for the entire screen image can be attained. The signal correction by multiplication is illustrated as an example herein. However, when the sensitivity correction coefficients indicated in FIG. 5e is stored as reciprocals, signal correction is performed by division. Accordingly, multiplication or division is adopted so as to reduce noise. In this way, noise components caused by sensitivity variations or the like can be eliminated from the image signal.

Although an example of sensitivity variation correction after dark current correction is illustrated in the above explanation, dark current correction may be performed after sensitivity correction. When there is not much noise, either of the two corrections may be performed.

In addition, although one line of data is taken as an example of the dark current correction data indicated in FIG. 5b and the sensitivity correction data indicated in FIG. 5e, several lines of data or the correction data for the entire screen image may be stored in the reference memory 37. Alternatively, the original correction data thinned out appropriately by sampling may be stored so that all correction data can be reproduced later by interpolation.

Furthermore, although an example of correcting the image signal having been stored once in the image memory 36 after tomographic imaging is described above, the image signal being outputted every moment from the X-ray imaging device 3 during X-ray imaging may be corrected. Moreover, the image signal to be outputted from the image memory 36 to the image display apparatus 38 may be corrected.

Additionally, since the dark current of the CCD sensor 3c depends on temperature, more accurate signal correction can be performed by measuring the temperatures of the CCD sensors 3c with the temperature sensor 40 provided in the X-ray imaging sensor 3 and by correcting the dark current correction data stored in the reference memory 37 and indicated in FIG. 5b in consideration of the deviation between the temperature at the time of the preparation of the dark current correction data and the temperature during X-ray imaging. It is believed that the temperature dependence of the dark current of the CCD sensor is nearly doubled each time the temperature rises by 6° C. Accordingly, when the temperature at the time of obtaining the dark current correction data is $T_0$ and when the temperature during actual imaging is T, the dark current correction data multiplied by the value of the equation shown below is used as new correction data.

[Equation 1]

$$2^{(T-T_0/6)}$$

Further, to previously store temperature $T_0$ measured when the dark current correction data is obtained, the storage region for temperature $T_0$ may be reserved in the reference memory 37. A temperature memory 41 may be provided separately as shown in FIG. 4.

The dark current of the CCD sensor tends to increase when the time during which the signal charges stay in each vertical shift register is prolonged. To correct the effect caused by this prolongation, the standard staying time $t_0$ of the signal charges in each vertical shift register is measured beforehand and stored in the reference memory 37 or the like, actual staying time t is measured, the dark current correction data is multiplied by coefficient $t/t_0$, and then the obtained data can be used as new correction data.

The invention may be embodied in order specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A medical X-ray imaging apparatus comprising:

an X-ray generator for emitting X-ray toward a subject;

an X-ray imaging device for detecting an X-ray image passed through the subject;

a swivel member for rotating the X-ray generator and the X-ray imaging device disposed opposingly around the subject;

an image memory for storing an image signal from the X-ray imaging device;

means for displaying the image signal stored in the image memory;

a first reference memory for storing as first correction data at least one line of data from the signal outputted by the X-ray imaging device while the X-ray imaging device is operated with no X-ray beam incident; and a second reference memory for storing as second correction data at least one line of data from the signal outputted by the X-ray imaging device while the X-ray imaging device is operated with an X-ray incident beam having nearly uniform intensity distribution, wherein the X-ray imaging device contains CCD sensors each of which is provided with a plurality of light-receiving pixels arranged in two dimensions, and takes the image of a predetermined tomographic plane by changing the frequency of a change transfer clock signal in accordance with the rotation speed of the swivel member;

and the image signal is corrected through addition or subtraction by the use of the first correction data stored in the first reference memory or through multiplication or division by the use of the second correction data stored in the second reference memory.

2. The medical X-ray imaging apparatus according to claim 1, wherein the signal correction is conducted on the image signal outputted from the X-ray imaging device.

3. The medical X-ray imaging apparatus according to claim 1, wherein the signal correction is conducted on the image signal stored in the image memory.

4. The medical X-ray imaging apparatus according to claim 1, wherein the signal correction is conducted on the image signal outputted from the image memory to the display means.

5. The medical X-ray imaging apparatus according to claim 1, wherein the first reference memory stores correction data for the entire screen image included in the signal outputted from the X-ray imaging device.

6. The medical X-ray imaging apparatus according to claim 1, wherein, a temperature sensor is further provided to detect the temperature of the X-ray imaging device and the signal correction is performed after the correction data of the first reference memory is corrected in accordance with the temperature detected by the temperature sensor.

7. The medical X-ray imaging apparatus according to claim 1, wherein the signal correction is performed after the correction data of the first reference memory is corrected in accordance with the staying time of signal charges in a vertical shift register of the CCD sensor.

* * * * *